(12) United States Patent
Matusch

(10) Patent No.: US 9,415,166 B2
(45) Date of Patent: Aug. 16, 2016

(54) CYLINDER-PISTON UNIT WITH ADHESIVE DISC II

(71) Applicant: Rudolf Matusch, Marburg (DE)

(72) Inventor: Rudolf Matusch, Marburg (DE)

(73) Assignee: LTS LOHMANN THERAPIE—SYSTEME AG, Andernach (DE)

( * ) Notice: Subject to any disclaimer, the term of this patent is extended or adjusted under 35 U.S.C. 154(b) by 3 days.

(21) Appl. No.: 14/276,151

(22) Filed: May 13, 2014

(65) Prior Publication Data

US 2014/0249471 A1 Sep. 4, 2014

Related U.S. Application Data

(63) Continuation-in-part of application No. PCT/EP2012/072579, filed on Nov. 14, 2012.

(30) Foreign Application Priority Data

Nov. 16, 2011 (DE) .......................... 10 2011 119 055

(51) Int. Cl.
*A61M 5/30* (2006.01)

(52) U.S. Cl.
CPC ................ *A61M 5/30* (2013.01); *A61M 5/3007* (2013.01); *A61M 2005/3022* (2013.01); *A61M 2205/19* (2013.01)

(58) Field of Classification Search
CPC . A61M 5/30; A61M 5/3007; A61M 5/14248; A61M 5/2046; A61M 5/2459; A61M 2005/1585; A61M 2005/3022; A61M 2005/14252; A61M 2205/19; A61M 2039/027; A61M 2039/066; A61M 2039/0081
See application file for complete search history.

(56) References Cited

U.S. PATENT DOCUMENTS

| | | | |
|---|---|---|---|
| 5,851,197 A * | 12/1998 | Marano et al. ................ 604/135 |
| 6,213,977 B1 | 4/2001 | Hjertman |
| 6,890,319 B1 | 5/2005 | Crocker |
| 2002/0193740 A1 | 12/2002 | Alchas et al. |
| 2003/0014006 A1 | 1/2003 | Alexandre et al. |
| 2007/0021716 A1 | 1/2007 | Hansen |
| 2007/0027427 A1* | 2/2007 | Trautman ............. A61B 17/205 604/46 |
| 2008/0287885 A1 | 11/2008 | Hoffmann et al. |
| 2009/0099510 A1 | 4/2009 | Poulsen |
| 2009/0227942 A1* | 9/2009 | Stroem Hansen et al. ...... 604/68 |
| 2010/0298767 A1* | 11/2010 | Bates ................... A61M 5/2459 604/72 |
| 2011/0166520 A1 | 7/2011 | Iwase et al. |
| 2011/0214777 A1 | 9/2011 | Matusch |
| 2011/0270217 A1 | 11/2011 | Stroem Hansen et al. |

FOREIGN PATENT DOCUMENTS

DE         698 36 594 T3     5/2010

\* cited by examiner

*Primary Examiner* — Nathan R Price
*Assistant Examiner* — Justin L Zamory
(74) *Attorney, Agent, or Firm* — R. S. Lombard

(57) ABSTRACT

A cylinder-piston unit, with at least one cylinder accommodating an injection solution, at least one piston, and an adhesive coating arranged in the area of the free end face of the cylinder. The cylinder has a bottom portion, on which a discharge tube is arranged. An adhesive disc, which is displaceable in the direction of the center line of the cylinder-piston unit between an installation position and an application position, is arranged on the discharge tube and/or on the bottom portion. On its end face directed away from the bottom portion, the adhesive disc has an adhesive coating. In the storage position, the adhesive disc has at least one sealing element or a sealing area for closing the discharge tube, the effect of which sealing element or sealing area is no longer present in the application position.

12 Claims, 5 Drawing Sheets

CYLINDER-PISTON UNIT WITH ADHESIVE DISC II

CROSS-REFERENCE TO RELATED APPLICATION

This is a continuation-in-part application of pending international application PCT/EP2012/072579 filed Nov. 14, 2012 and claiming the priority of German Application No. 10 2011 119 055.8 filed Nov. 16, 2011 which is hereby incorporated herein by reference in its entirety as though fully set forth

BACKGROUND OF THE INVENTION

The invention relates to a cylinder-piston unit of a needle-free injector, with at least one cylinder accommodating an injection solution, at least one piston, and an adhesive coating arranged in the area of the free end face of the cylinder.

DE 10 2005 054 600 discloses a cylinder-piston unit of a needle-free injector, of which the cylinder has, at its front end face, a sealing film fixed by means of a pressure-sensitive adhesive The pressure-sensitive adhesive has a greater affinity to the end face of the cylinder than to the sealing film, such that, after the sealing film has been pulled off, the pressure-sensitive adhesive remains in place in order, during the injection, to fix the skin of the patient with respect to the injector.

DE 698 36 594 T3 describes a device for transcutaneous placement of a flexible cannula at a medicament admission site on the patient. For this purpose, the device has an adapter set, and a spring accumulator that can be tensioned and that is accommodated in a housing. The adapter set, which can be inserted from the front into the housing, is principally composed of an adhesion plate, a flexible cannula and an insertion needle. When the device is triggered, the adapter set is positioned on the skin by means of the relaxation of the spring accumulator. The cannula is pushed under the skin with the aid of the insertion needle. After the housing has been removed and the insertion needle pulled out, the infusion can begin.

In needle-free injections, the injection solution must be administered by a high-velocity jet through the skin of the patient. The upper layer of the skin constitutes a strong mechanical covering of the skin layers lying below it and protects them from external influences. It is composed of keratinized cells which lie alongside and over one another, the interstices being lined by lipids.

In the context of a modular injector, the object of the present invention is therefore to develop a cylinder-piston unit whose discharge system is suitable for safely penetrating the outer layers of skin covered by the term "dermis", or possibly also the other layers, in order to convey the injection solution into or under the skin and keep it there for a definable period of time.

SUMMARY OF THE INVENTION

This object is achieved, according to the invention, by the features of claim 1. To this end, the cylinder has a bottom portion, on which a discharge tube is arranged. An elastic adhesive disc, which is displaceable in the direction of the centre line of the cylinder-piston unit between an installation position and an application position, is arranged on the discharge tube and/or on the bottom portion. On its end face directed away from the bottom portion, the adhesive disc has an adhesive coating for affixing to the skin. In the storage position, the adhesive disc has at least one sealing element or a sealing area for closing the discharge tube, the effect of which sealing element or sealing area is no longer present in the application position. In order to indent the skin without damaging it, the front edge of the free end face of the discharge tube protrudes, in the application position, at least 0.5 mm beyond the adhesive coating of the adhesive disc. The skin can be tensioned by the expansion of the adhesive disc and the protrusion of the discharge tube. After the cylinder-piston unit has been taken way, the adhesive disc remaining on the skin can be removed separately.

Here, the cylinder-piston unit of a needle-free injector, for example, is proposed by the invention. The injector, which can also be a disposable injector, not only accommodates the cylinder-piston unit but also a drive mechanism that is installed in an injector housing and that acts on a piston-actuating ram. As possible drive mechanisms, it is possible to use spring accumulators, gas drives with openable gas cartridges, or pyrotechnic drives. Known spring energy accumulators use pretensioned mechanical or pneumatic springs or spring systems. If a spring energy accumulator is used as drive mechanism, the piston-actuating ram is held with a form fit, via at least one support rod or draw hook arranged on or in the injector housing, in order to pretension and hold this spring energy accumulator. The one or more support rods or draw hooks are retained in their locked position by means of one or more trigger elements until the use of the injector. To trigger the injector, the one or more support rods or draw hooks are released, such that the piston-actuating ram, under the effect of the spring energy accumulator, can move at least approximately parallel to the centre line of the injector, with the result that the injection solution present in the cylinder of the cylinder-piston unit is expelled via at least one nozzle.

In the present case, an adhesive disc, displaceable on the cylinder, is mounted in front of the cylinder-piston unit. When the ready-to-use injector is placed onto the skin of the patient, the skin of the patient adheres, in a first step, to the adhesive disc sitting on the cylinder in an installation position. At this stage, the adhesive disc keeps the cylinder closed as before. By further pressing the injector onto the skin, the adhesive disc slips, pushing open the sealing means integrated in the adhesive disc. After the desired displacement of the adhesive disc, a discharge tube integrally formed or secured on the cylinder protrudes beyond said disc and, as a result of this protrusion, tensions the skin in the area of the nozzle of the cylinder.

The tensioning of the upper layer of skin in the area of the outlet nozzle leads to a two-stage pulling-apart of the keratinized cells of the horny layer of the skin. The first stage involves stretching of the skin at the moment when the discharge tube passes through the adhesive layer of the adhesive disc. The second stage involves partially pressing the skin away from the adhesive disc. The associated indentation of the skin causes an additional stretching of the skin. In this way, penetration of the injection jet is made easier during the administration.

BRIEF DESCRIPTION OF THE DRAWINGS

Further details of the invention will become clear from the dependent claims and from the following descriptions of schematically depicted illustrative embodiments.

DETAILED DESCRIPTION OF THE PARTICULAR EMBODIMENTS

Figure 1:
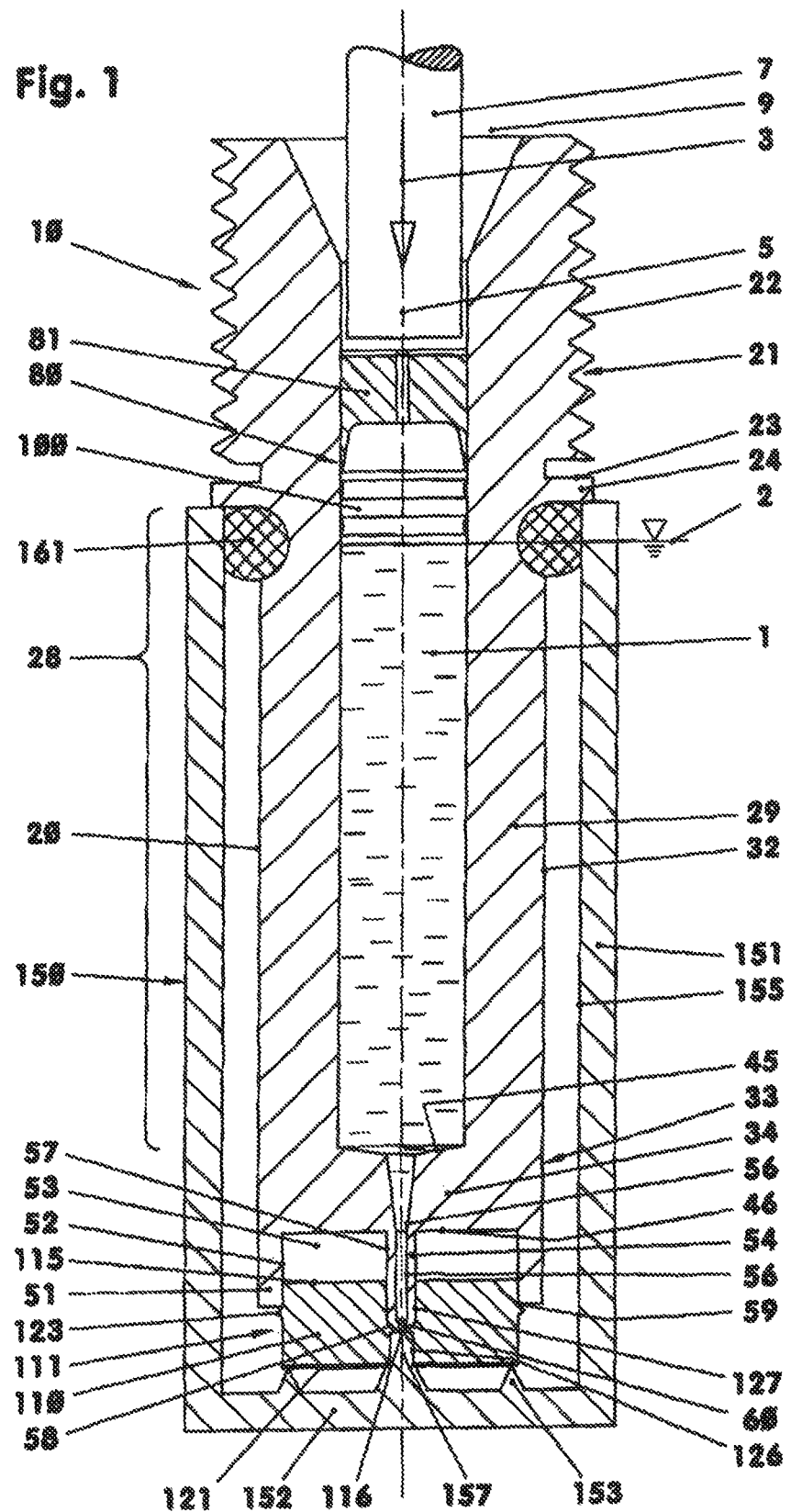
FIG. 1 shows a cylinder-piston unit with integrally formed discharge tube and protective housing.

FIG. 1 shows a cylinder-piston unit (10) of a needle-free injector. The cylinder-piston unit (10) is composed of a cylinder (20) and a piston, for example a two-part piston (80). The cylinder (20) is additionally surrounded, for example, by a protective housing (150).

Above the piston (80), the lower part of a piston-actuating ram (7) is shown, which belongs to the injector (not depicted here). The cylinder (20) is secured on the injector by means of its outer thread (22), present in the rear area of the cylinder, or by means of slits (23). In the area of the cylinder bottom, an adhesive disc (110) is also arranged between the cylinder (20) and the protective housing (150).

The for example one-part cylinder (20) is composed of a housing adapter (21), a tube portion (28) and a bottom portion (33). With the housing adapter (21), the cylinder (20) is fixed in an injector housing (not depicted). For this purpose, its radial outer wall has an outer thread (22) and/or at least two slits (23) lying opposite each other. The slits (23) have a depth of 2 mm, for example. They are located at the thread end in immediate proximity to the tube portion (28). The width of the slits (23) is 0.6 mm, for example.

Between the slits (23) and the tube portion (28), there is an abutment web (24), of which the external diameter can be identical, for example, to the outer diameter of the thread. The external diameter of the tube portion (28) is more than twice as great as the diameter of the inner wall (31). It is dimensioned such that its material withstands at least a pressure load of $350*10^5$ Pa (pascals).

The housing adapter (21) is adjoined by the cylinder wall (29) of the tube portion (28). Along the length of the tube portion, the cylinder wall (29) has, for example, a constant wall thickness of 3.25 mm.

The bottom portion (33) has an outwardly plane bottom plate (34), which corresponds to the mean wall thickness of the cylinder wall (29) in the area of the tube portion (28). An annular web (51), e.g. in the shape of a cylindrical tube, is integrally formed in the outer area of the bottom plate (34). The annular web (51), which encloses a receiving space (53) for the adhesive disc, is, for example, as high as the wall thickness of the bottom plate (34). The wall thickness of the annular web (51) is about one third of the wall thickness of the cylinder wall (29) of the tube portion (28).

The discharge tube (54) supporting the outlet nozzle (60) is arranged in the centre of the plane bottom plate (34). The discharge tube (54), of which the external diameter measures 2.25 mm for example, has a front end which protrudes about one millimeter beyond the annular web (51). Lying between the at least approximately cylindrical outer wall of the discharge tube (54) and the cylindrical inner wall (52) of the annular web (51), there is a receiving space (53), e.g. with a depth of 3 mm, for the adhesive disc.

The end face (58) of the discharge tube (54) is spherically curved, at least in part, or plane. The outlet nozzle (60) lying to the front has an internal diameter of 0.2 to 0.4 mm, whereas the internal diameter of the bore (56) leading to the outlet nozzle (60) measures about 0.5 to 1 mm, at least in its front half.

Figure 2:
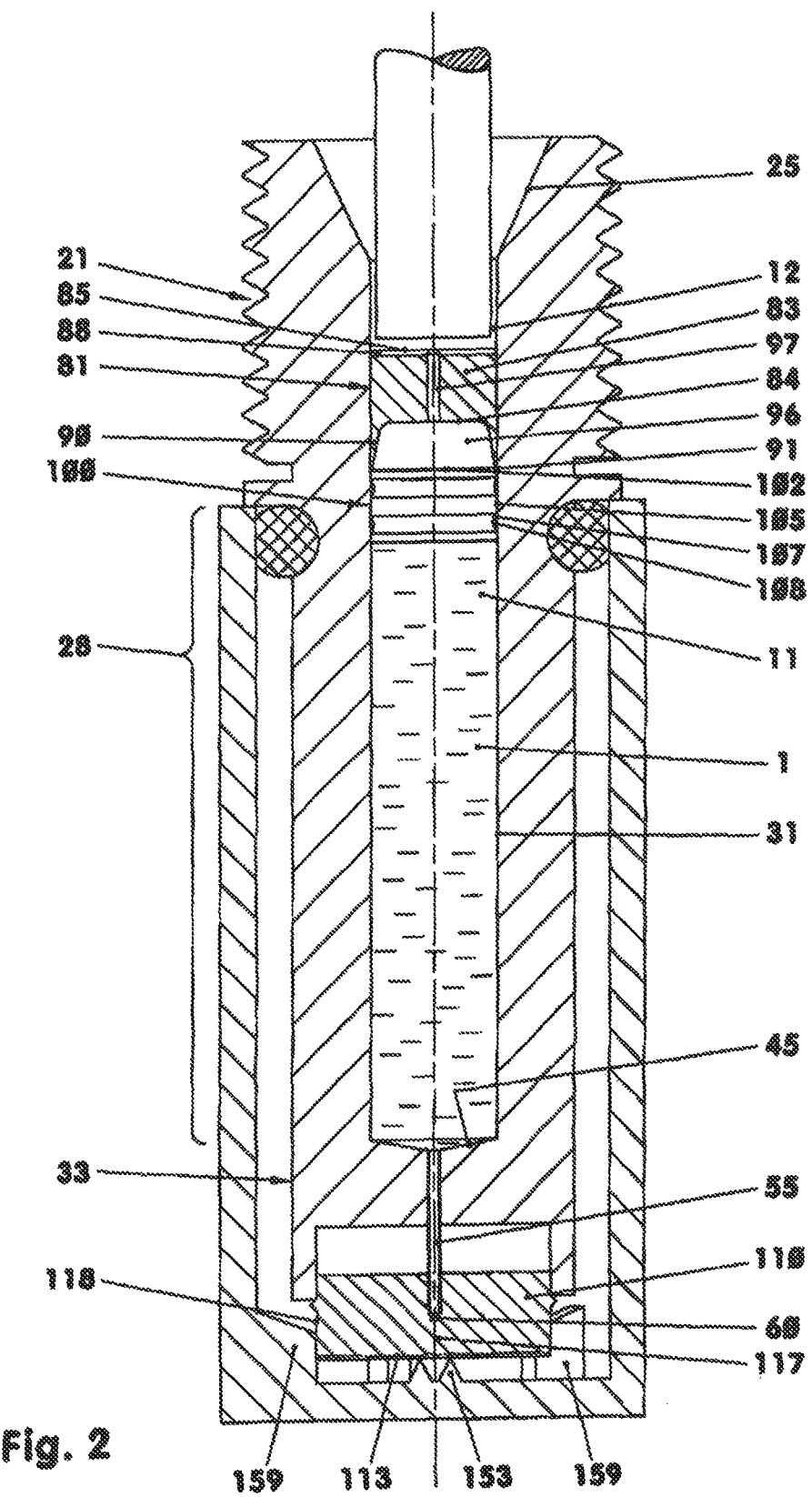
FIG. 2 shows the same as FIG. 1, but with a metallic discharge tube.

According to FIG. 2, the inner wall (31) of the cylinder is shaped cylindrically, at least in the tube portion (28). It there has an internal diameter of 5.5 mm, for example. In the area of the housing adapter (21), the inner wall (31) of the cylinder widens out in the shape of a truncated cone. The cone angle of this widening (25) is 50 degrees, for example. The length of the widening (25) corresponds to about one third of the length of the housing adapter (21).

In the area of the bottom portion (33), the inner wall (31) of the cylinder ends in a cylinder bottom (45), of which the cone angle measures 160 degrees for example. According to FIG. 1, a discharge bore (56) is located between the cylinder bottom (45) and the outlet nozzle (60) arranged in the discharge tube (54), said discharge bore (56) having a cylindrical wall at least in the area before the outlet nozzle (60). In the illustrative embodiment, the rear portion of the bore (56) directed towards the cylinder bottom (45) is designed as a truncated cone. It has a cone angle of 12 degrees, for example. It extends, for example, in the area of the wall of the bottom plate (34).

Figure 7:
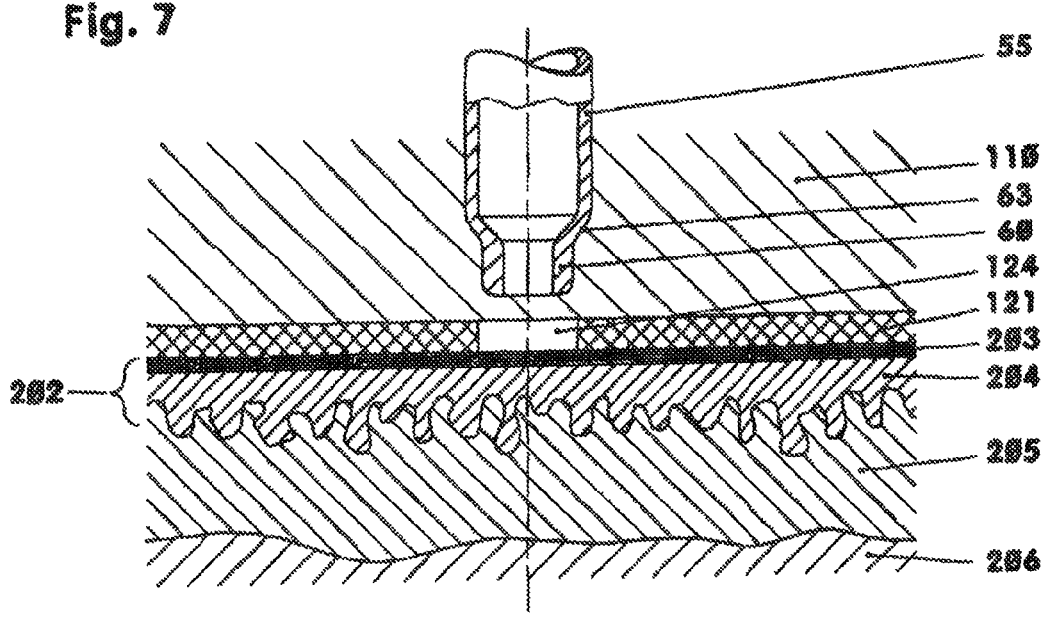
FIG. 7 shows a cross section of the metallic discharge tube after it has been placed onto the skin of the patient, before complete piercing of the adhesive disc.

Instead of the integrally formed discharge tube (54), it is also possible to use a thin-walled tube (55) (cf. FIG. 2), at the front end of which an outlet nozzle (60) is arranged. The thin-walled tube (55), which is produced for example from a stainless steel, has an external diameter of 0.5 mm, for example. The wall thickness of the discharge tube (55) behind the outlet nozzle (60) measures 0.05 mm, for example. The nozzle diameter, or the internal diameter of the discharge tube (55), generally corresponds to the values known from the previous variant. According to FIGS. 7 and 8, the internal diameter measures 0.2 mm for example, while the external diameter measures 0.36 mm. In order to produce this outlet nozzle (60), the front area of the discharge tube (55) is reduced to a length of ca. 0.325 mm by material compression The free nozzle end is rounded with a radius of 0.05 mm, for example, so as not to damage the skin (200) during use.

According to FIG. 1, an adhesive disc (110) is arranged between the discharge tube (54) and the annular web (51), in the front area of the receiving space (53) for an adhesive disc. It has a material thickness that is at least 0.5 mm greater than the depth of the receiving space (53) for the adhesive disc. The adhesive disc (110) has two central blind bores (126, 127) in opposite directions. Both blind bores (126, 127) end, in the middle area of the adhesive disc (110), before a forwardly bulging, thin-walled membrane (116) serving as sealing element. The rear blind bore (127) sealingly surrounds the front area of the discharge tube (54) and bears tightly thereon. The membrane (116) sits with a snug fit, like a cap, on the optionally spherically curved front end face (58) of the discharge tube 54. Its wall thickness is 0.13 mm, for example. According to FIG. 1, as a result of the lack of expansion by the discharge tube (54), the front blind bore (126) has a diameter that is ca. 0.5 to 1 mm smaller than the diameter of the rear blind bore (127).

For the cylinder variant with the cemented-in or encapsulated discharge tube (55), an adhesive disc (110) is used that has no bore. The area of the adhesive disc (110) located in front of the discharge tube (55) serves as a sealing area (117) replacing the membrane (116).

The substantially cylindrical outer wall of the adhesive disc (110) is guided on the cylindrical inner wall (52) of the annular web (51). According to FIG. 1, the adhesive disc (110) has, in the upper area of its outer wall, a circumferential web (123) which protrudes radially, e.g. by 0.5 mm, and via which the adhesive disc bears elastically on the front inside edge (59) of the annular web (51).

For positioning the adhesive disc (110) on the annular web (51) of the bottom portion (33), the latter can also have a radially inwardly protruding web, which is integrally formed in the front area of the annular web (51) and which protrudes elastically into a corresponding annular groove of the adhesive disc (110).

The adhesive disc (110) is made of rubber, for example, or of another elastomer and is provided, on its plane front end face, with an adhesive layer (121) composed, for example, of a pressure-sensitive adhesive. The rest of the surface areas have good sliding ability, since the adhesive disc (110) is at least partially treated with silicone oil or coated with Teflon. In the variant suitable for the discharge tube (54) (cf. FIGS. 1, 3 and 4), the adhesive layer (121) is omitted in the area of the bore (126). In the variant for the metallic discharge tube (55), the adhesive layer (121) can have a central recess (124), of which the diameter is at least greater than the external diameter of the discharge tube (55) in the area of the outlet nozzle (60) (cf. FIG. 7).

The pressure-sensitive adhesive of the adhesive disc (121) is such that its adhesion force with respect to the adhesive disc (110) is at least 50% greater than with respect to a disinfected skin surface (201).

Figure 3:
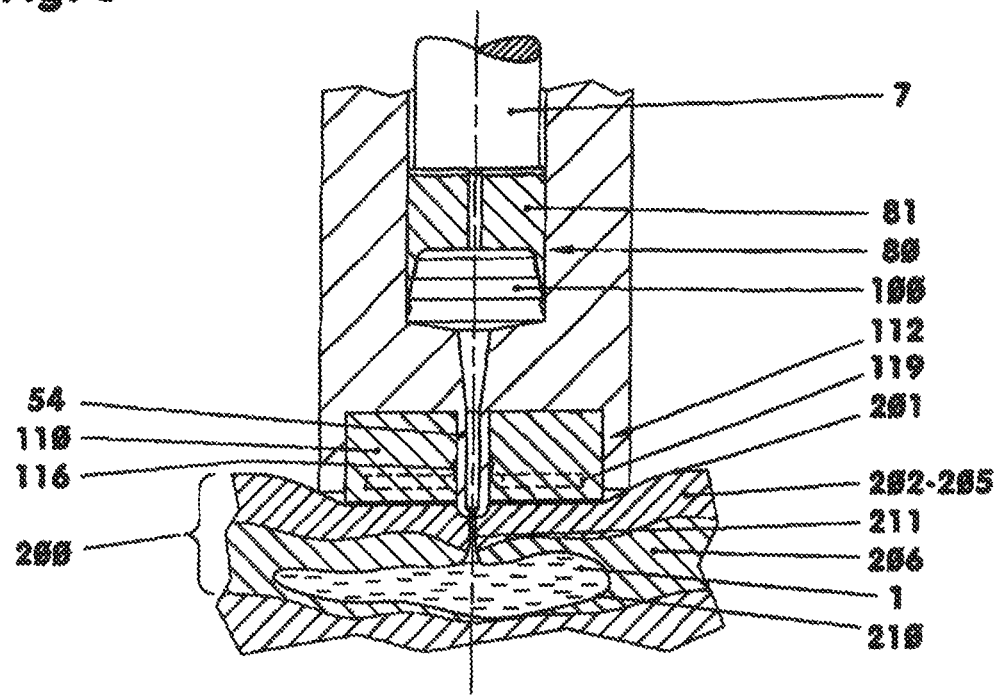
FIG. 3 shows a cross section through the front area of the cylinder-piston unit with integrally formed discharge tube, after the injection solution has been dispensed.
Figure 4:
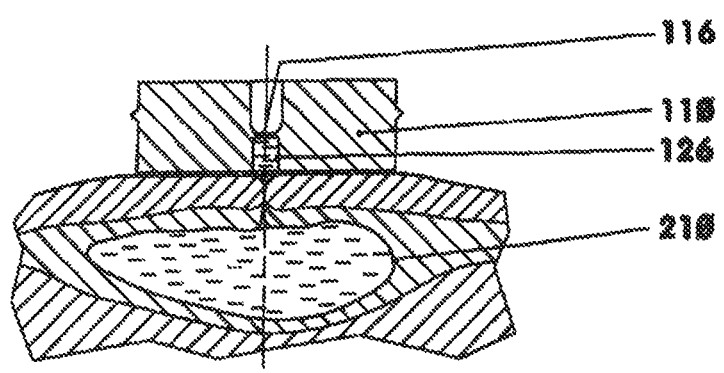
FIG. 4 shows a cross section through the skin closed again with the adhesive disc according to FIG. 1 and FIG. 3.

A stiffening disc (119) can be inserted into the adhesive disc (110). It is shown in FIG. 3 by broken lines. This stiffening disc (119), e.g. encapsulated or vulcanized in, has a wall thickness of 0.5-1 mm, for example. It is made from a conventional ferrous or non-ferrous metal, for example. Its bore is at least 1 mm larger than the external diameter of the discharge tube (54). The external diameter of the stiffening disc (119) is, for example, 1-2 mm smaller than the external diameter of the adhesive disc (110). The stiffening disc (119), here integrated into the adhesive disc (110), is positioned for example 0.5 to 1 mm behind the front adhesive layer (121). The centre lines of the adhesive disc (110) and of the stiffening disc (119) are congruent.

If appropriate, the adhesive disc (110) has at least one lateral notch, which is oriented parallel to the centre line (5) and by means of which, upon insertion of the adhesive disc (110) into the receiving space (53), the air present therein can be easily displaced. The air can also escape via a bore arranged in the annular web (51), in proximity to the end face (46) of the bottom portion (33).

According to FIGS. 1 and 2, a pot-shaped protective housing (150), a sterile closure, surrounds the tube portion (28) and the bottom portion (33) with the inserted adhesive disc (110) of the cylinder (20). It consists here of a tubular jacket (151) and a plane bottom (152). In the illustrative embodiments shown, the protective housing (150), on account of its shape, is made from the plastics material cyclo-olefin copolymer (COO). This material has a particularly low permeability to gas and water vapour. With a simpler shape, the protective housing (150) can be made of glass.

In the area of the tube portion (28), the distance between the outer wall (32) of the tube portion (28) and the inner wall (155) of the protective housing (150) is 1.5 mm, for example. The axial distance between the bottom (152) of the protective housing (150) and the adhesive disc (110) measures 1 mm, for example, according to FIG. 1.

The protective housing (150) is fixed releasably on the cylinder (20) at two locations. The first location lies at the transition between the tube portion (28) and the abutment web (24) of the cylinder (20). There, according to FIG. 1, an O-ring (161) sits in a notch of the cylinder (20) and seals the protective housing (150) in relation to the cylinder (20). At the same time, the O-ring (161) centres the protective housing (150) on the cylinder (20). Instead of a conventional O-ring (161), it is also possible to use a quad ring, a profiled ring or the like.

Upon assembly, the sealing ring (161) is clamped between the protective housing (150) and the cylinder (20), such that, in addition to the sealing function, it can also easily perform a centring and holding function. If appropriate, the sealing ring (161) can also be replaced by a tough sealing adhesive.

The second location for supporting the protective housing (150) on the cylinder (20) is situated centrally in the bottom (152) of the protective housing (150). There, a central supporting stub (157) is arranged, which protrudes so far into the blind bore (126) of the bottom portion (33) that it makes contact with the membrane (116) there. The supporting stub (157) fixes the front end of the protective housing (150) radially over the adhesive disc (110), which bears on the annular web (51) of the cylinder (20).

For axial support of the adhesive disc (110), the bottom (152) is additionally provided with an annular supporting web (153), which bears with its upper circular edge on the adhesive disc (110), in the edge region of the latter. The edge is so narrow that it develops only a slight adhesion force with respect to the adhesive disc (110).

To be able to support the protective housing (150) in the front area on the cylinder (20) also in the radial direction in the variant according to FIG. 2 with the steel discharge tube (55), the protective housing (150) has, for example, five radially oriented supporting ribs (159). These supporting ribs (159), distributed equidistantly on the circumference of the jacket (151), are, for example, integrally formed on the bottom (152) and on the jacket (151). The supporting ribs (159) have radial inner faces via which they bear on the cylindrical outer face (118) of the adhesive disc (110).

According to FIGS. 1 and 2, the cylinder (20) is partially filled with an injection solution (1). The liquid level (2) of the injection solution (1) is situated in the transition area between the housing adapter (21) and the tube portion (28). A disc-shaped sealing body (100) is placed on the liquid level (2) in a sterile manner and without bubbles and, under the effect of radial clamping, bears sealingly on the inner wall (31) of the cylinder. A pot-shaped drive body (81) is arranged behind the sealing body (100). The drive body (81) bears partially on the sealing body (100) or is at a distance of, for example, 0.2 to 0.5 mm therefrom.

The sealing body (100) here is a disc whose undeformed diameter is, for example, twice as great as its disc thickness. On its circumference, the disc (100) can have a grooved profile (107) with, for example, two grooves (108) (cf. FIG. 2). The grooved profile (107) is, for example, configured here such that the sealing body (100) has, in cross section, a wave line with two wave valleys forming the grooves (108). The wave line is composed here of arcs of a circle.

Since the sealing body (100) is an elastomer body, the wave crests of the sealing disc are flattened off (cf. FIGS. 1, 2, 4 and 6).

The pot-shaped drive body (81), whose length corresponds to its external diameter for example, is composed of a disc-shaped impact plate (83) and of a skirt (90) formed integrally thereon. The thickness of the impact plate (83) is here slightly greater than the length of the skirt (90) (cf. FIG. 2).

The impact plate (83), which is impacted by the piston-actuating ram (7) when the injector is triggered, has at least a for example central bore (97), by which the cylinder chamber areas (11, 12) located in front of and behind the drive body (81) are connected to each other with minimal restriction. According to the illustrative embodiments, the bore (97), of which the minimum diameter is between 1 and 2 mm, ends on the rear face (85) of the drive body (81), e.g. in a channel intersection (88) composed of two channels intersecting in the area of the bore (97). The channels of the channel intersection (88) each have, for example, a semicircular cross section, wherein the diameter of the cross sections corresponds, for example, to the diameter of the bore.

The front face (84) of the impact plate (83) is adjoined by the skirt (90), which is designed as an elastic sealing lip. Starting from the front face (84), the wall of the skirt (90) tapers towards the front outer sealing edge (91), which bears elastically on the inner wall (31) of the cylinder in each operating state of the injector. In the installed state, the skirt (90) and the front face (84) enclose an immersion space (96). The latter has substantially the shape of a truncated cone, of which the cone angle measures 20 degrees, for example.

The piston (80), i.e. the combination of the drive body (81) and of the sealing body (100), permits simple bubble-free, sterile filling and closure of the cylinder-piston unit (10) in connection with an ejection procedure upon release of the injector, which withstands a very high compression pulse of up to $350*10^5$ Pa.

When the injector is ready for the injection, the protective housing (150) is pulled off from the front of the cylinder (20), e.g. by manual force. In doing this, the adhesive disc (110) remains in the bottom portion (33) of the cylinder (20). The sealing ring (161) also remains on the outer wall (32) of the cylinder (20).

To be able to administer the injection solution, the injector, with the adhesive disc (110) towards the front, is placed onto the skin surface (201) of the patient. The adhesive disc (110), which is still located in its installation position (111), affixes itself to the skin surface (201) via its adhesive layer (121) which, for example with a diameter of 10 mm, has a surface area of ca. 75 mm². According to the illustrative embodiment in FIG. 1, only the centre of the adhesive disc (110) is not equipped with an adhesive layer (121). The location free of the adhesive layer has a diameter of 1 to 2 mm, for example.

By means of the pressing force of the injector, the adhesive disc (110) is loaded in such a way that, with the locking action of the circumferential web (123) being overcome and the membrane (116) being torn open, it moves along the discharge tube (54) in the direction of the bottom portion (33). While the front end face (58) of the discharge tube (54) moves towards the skin, the discharge tube (54) expands the front blind bore by ca. 0.5-1 mm. This expansion has the effect that the layer of skin affixed to the adhesive layer (121) is actively pretensioned in a first stage, solely by the widening of the blind bore (126).

In the subsequent forward movement of the injector, the adhesive disc (110) slips further into the receiving space (53) for the adhesive disc, so as to bear with its rear face (115) on the end face (46) of the bottom portion (33). The adhesive disc (110) is now located in its application position (112). It now completely fills the receiving space (53) for the adhesive disc.

This further travel of the adhesive disc (110) means that, on the one hand, the adherence between the adhesive layer (121) and the skin of the patient is strengthened by the increased contact pressure, and, on the other hand, the discharge tube (54) protrudes a few tenths of a millimeter from the adhesive disc (110) (cf. FIG. 3).

The front end (58) of the protruding discharge tube (54), with the for example almost spherically curved front face (58), forces a depression into the skin (200), as a result of which the second stage of the skin expansion begins. The resulting indentation depth, which is the distance between the lower adhesive layer (121) and the most forward point or the most forward edge of the discharge tube (54), corresponds, for example, to half the external diameter of the discharge tube (54). In this case, the skin surface (201) in the area of the front face (58) of the discharge tube (54) is actively expanded in total by ca. 100%.

If the injector from FIG. 2 is used, there is in principle a comparable two-stage stretching of the skin as in the example according to FIG. 1. On account of the relatively slender discharge tube (55) with its tapering (63) in the area of the outlet nozzle (60), there are, depending on the skin type, two different contact conditions for the skin (200) to be stretched.

In a first contact condition, when the discharge tube (55) emerges, the skin (200) nestles on the outer wall (57), such that the surface (201) of the stretched skin (200) assumes the shape of a stepped tin, wherein the stepped tin shape comes about through the tapering (63) of the discharge tube (55). In the two-stage skin expansion, this variant results, for example, in an expansion factor of 3.5 to 4.

In a second contact condition, the horny layer (203) is lifted away or detached from the adhesive layer (121) in part by the outlet nozzle (60), without damaging the skin (200). The lifting area has, for example, a diameter (207) that can measure up to 1 mm.

Figure 8:
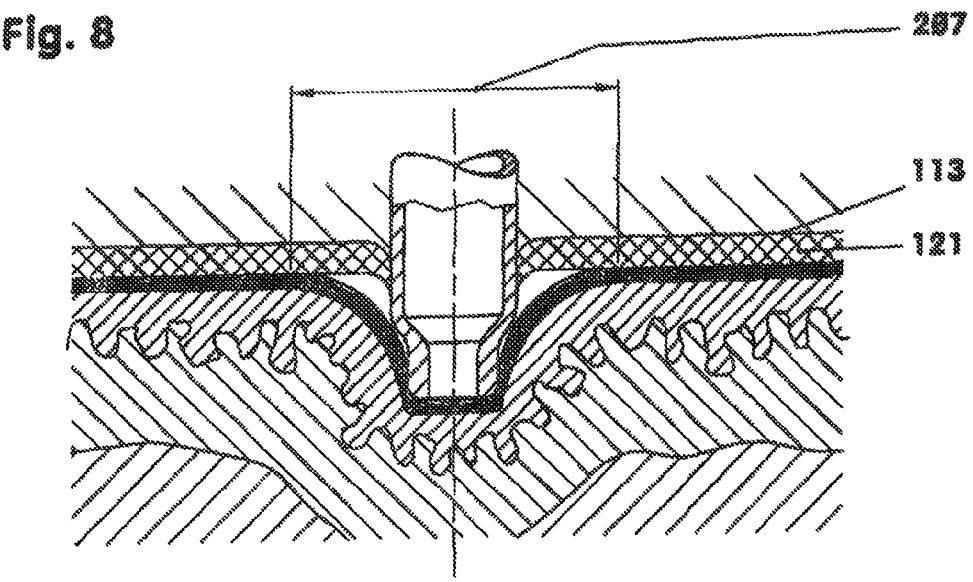
FIG. 8 shows the same as FIG. 7, but after complete piercing of the adhesive disc and tensioning of the patient's skin.

With greater expansion in the area around the outlet nozzle (6), the skin (200) will here assume a for example funnel-like configuration (cf. FIG. 8). Here, the epidermis (202) and the dermis (205) are indented into the subcutis (206). With the geometrical conditions according to FIG. 8, in which the indentation of the horny layer corresponds to about half the diameter (207) of the skin surface (201) detached from the adhesive layer (121), a horny-layer expansion of 60 to 70% is obtained there in the area of the funnel-like indentation.

At the same time, the injector is triggered by being pressed onto the skin (200). The piston-actuating ram (7), pretensioned by means of a mechanical or pneumatic spring, applies a sudden load to the piston (80), such that the injection solution (1) penetrates in a high-velocity jet through the tensioned skin of the patient.

The piston-actuating ram (7) first strikes with great force against the drive body (81), see arrow direction (3) in FIG. 1. The drive body (81) is pressed against the almost incompressible sealing disc (100) resting on the liquid level (2). The skirt (90) slides along the inner wall (31) of the cylinder via the profiled outer wall (105) of the sealing disc (100). The sealing disc (100) enters the immersion space (96) of the drive body (81), cf. FIGS. 3 and 5. The displaced air flows through the bore (97) and along the channel intersection (88) on the piston-actuating ram (7) into the external environment (9) of the injector.

The sealing disc (100) and the drive body (81) now form a virtually rigid combination, namely the piston (80), which pushes the injection solution (1) forwards. The sealing with respect to the inner wall (31) of the cylinder is taken over by the sealing edge (91) of the skirt (90), which is pressed on more strongly by the sealing disc (100) loaded by the pressure of the liquid. Since the coefficient of sliding friction of the sealing edge (91) is less than the coefficient of sliding friction of the sealing disc (100) because of the material used for the drive body, there is a low sliding-friction resistance despite the high sealing action.

Figure 5:
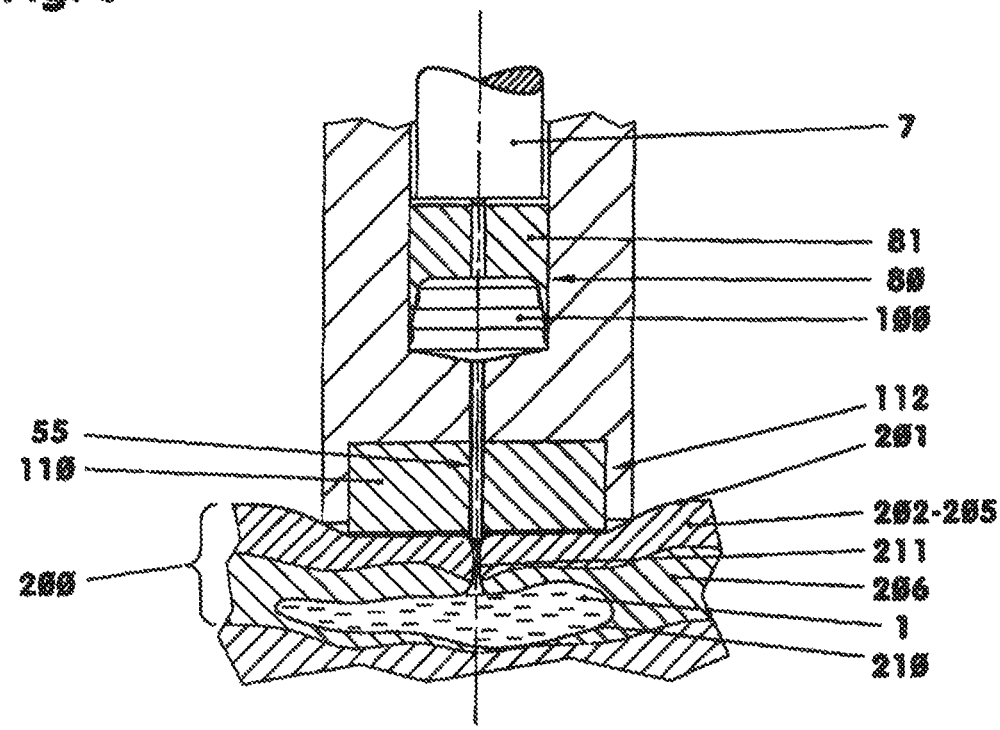
FIG. 5 shows the same as FIG. 3, but with a metallic discharge tube.

As a result of the high pressure of the liquid which, for example for subcutaneous injection at a flow velocity of ca. 150 m/sec, measures at least $250*10^5$ Pa, the liquid jet penetrates the epidermis (202) and the dermis (205), which together are up to 4 mm thick for example (cf. FIGS. 3 and 5). In subcutaneous injection, an inflow channel (211) generated by the liquid jet ends only in the subcutis (206). In the connective tissue of the subcutis (206), which is permeated by capillary vessels and is rich in adipose tissue, a for example discus-shaped pool (210) of injection solution then forms, which is fed by the liquid jet.

At least some of this pressurized pool (210) of injection solution will immediately empty via the inflow channel (211) when the injector with all its parts is lifted away from the skin (200). After the injector is taken away, this disruptive emptying is countered by the skin, by virtue of the fact that the skin expansion decreases again and for the most part closes the inflow channel (211), at least in the case of quite small injection quantities.

In the present case, after the injector has been taken away, the adhesive disc (110) additionally remains in place because of its adhesive layer (121), until it is separately removed at a later point. Until such time, however, its previously torn membrane (116) closes the blind bore (126) of the adhesive disc (110) on account of its curvature oriented counter to a possible outflow direction. A small subsidiary amount of the injection solution builds up possibly as loss in the front blind bore (126) in front of the membrane (116). The patient removes the adhesive disc (110), including the adhesive layer (121) adhering thereto, as soon as the injection-induced bulging of the skin has substantially receded.

Figure 6:
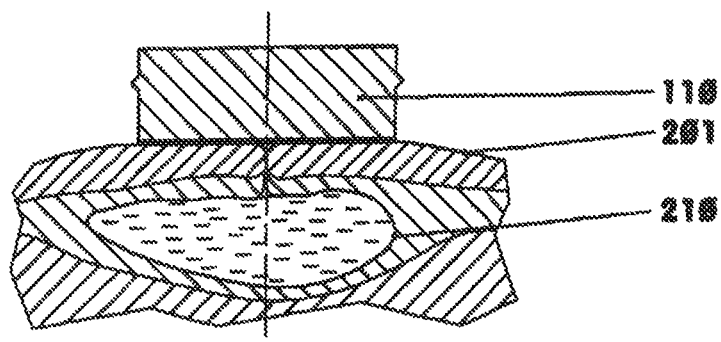
FIG. 6 shows a cross section through the skin closed again with the adhesive disc according to FIG. 2 and FIG. 5.

The variant according to FIG. 2 shows the same behaviour upon introduction of the injection solution, cf. FIG. 5. However, the external closure of the inflow channel (211) according to FIG. 6 is more effective than in the solution according to FIG. 4. Since, prior to the injection, the adhesive disc (110) is pierced only by the thin steel discharge tube (55), with the creation of a narrow channel, the latter completely closes immediately after the injector is taken away. Here too, the adhesive disc (110) is detached from the skin surface (201) only when the injection solution (1) has distributed in the tissue surrounding the pool (210) of injection solution.

LIST OF REFERENCE SIGNS

1 Injection solution
2 Liquid level
3 Arrow direction upon injector release
5 Centre line
7 Piston-actuating ram
9 Environment
10 Cylinder-piston unit
11 Cylinder chamber area in front of the piston
12 Cylinder chamber area behind the piston
20 Cylinder
21 Housing adapter
22 Outer thread
23 Slits
24 Abutment web
25 Widening on the inside
28 Tube portion
29 Cylinder wall
31 Inner wall, radial
32 Outer wall, radial
33 Bottom portion
34 Bottom plate
45 Cylinder bottom, inner side of the cylinder bottom
46 End face of the bottom portion, front
51 Annular web
52 Inner wall, cylindrical
53 Receiving space for adhesive disc
54 Discharge tube, plastic
55 Discharge tube, tube, steel tube
56 Bore, inner bore
57 Outer wall
58 Face, end face
59 Front edge
60 Nozzle, outlet nozzle
63 Tapering
80 Piston, combination of (81) and (100)
81 Drive body
83 Impact plate
84 Front face
85 Rear face
88 Channel intersection
90 Elastic skirt; sealing lip
91 Edge, sealing edge
96 Immersion space, hollow space
97 Recess, bore, central
100 Sealing body, sealing disc
102 Rear face
105 Outer wall, profiled
107 Grooved profile
108 Groove
110 Adhesive disc, elastomer disc
111 Installation position
112 Application position
113 Front face
115 Rear face
116 Sealing element, membrane
117 Sealing area
118 Outer face, radial
119 Stiffening disc
121 Adhesive layer, front, pressure-sensitive adhesive, adhesive coating
123 Circumferential web
124 Recess in (121)
126 Bore portion, front
127 Bore portion, rear
150 Protective housing, glass; outer shell; sterile closure
151 Jacket, tubular
152 Bottom, plane
153 Supporting web
155 Inner wall
157 Supporting stub
159 Supporting ribs
161 O-ring
200 Skin
201 Skin surface
202 Epidermis
203 Horny layer (stratum corneum)
204 Keratinization and regeneration layer
205 Papillary and reticular layer (dermis)
206 Subcutis
207 Diameter of the detached skin surface (201)
210 Pool of injection solution
211 Inflow channel

What is claimed is:

1. Cylinder-piston unit (10) of a needle-free injector, including at least one cylinder (20) for accommodating an injection solution and at least one piston (80), a piston-actuating rain (7) for actuating the at least one piston (80), and an adhesive coating (121) arranged in the area of a free end face of the cylinder (20), the improvement which comprises:

the cylinder (20) has a bottom portion (33), on which a discharge tube (54, 55) is arranged, the bottom portion (33) of the cylinder (20) has a front end face (46), an elastic adhesive disc (110), which is displaceable in the direction of a centre line (5) of the cylinder-piston unit (10) between an installation position (111) and an application position (112), is slidably arranged on the discharge tube (54, 55) and/or on the bottom portion (33), the bottom portion (33) has an annular web (51), which extends forwards in a continuation of the outer wall (32) of the cylinder (20), the annular web (51) has a cylindrical inner wall (52), the annular web (51) encloses a receiving space (53) for the elastic adhesive disc (110), the elastic adhesive disc (110) slideable within the receiving space (53), the elastic adhesive disc (110) in the installation position (111) having a first portion thereof occupying a front area of the receiving space (53) with the remainder of the receiving space (53) being unoccupied between the front end face (46) of the bottom portion (33) of the cylinder (20) and the elastic adhesive disc (110) and a second portion of the elastic adhesive disc (110) extending beyond the cylindrical inner wall (52), upon actuation of the at least one piston (80) the elastic adhesive disc (110) slips further into the receiving space (83), in the application position (112) the receiving space (53) being now fully occupied by the slideable elastic adhesive disc (110) with a third portion thereof extending beyond the cylindrical inner wall (52), the elastic adhesive disc (110) in the application position (112) bears on the front end face (46) of the bottom portion (33), the elastic adhesive disc (110), on its end face (113) directed away from the bottom portion (33), has the adhesive coating (121) for affixing to the skin (200) of a patient, the elastic adhesive disc (110), in the installation position (111), has at least one sealing element (116) or a sealing area (117) for closing the discharge tube (54, 55), and in the application position (112) the closing effect of the sealing element (116) or sealing area (117) is no longer present, a front edge (59) of a free end face (58) of the discharge tube (54, 55), in the application position (112) protrudes at least 0.5 mm beyond the adhesive coating (121) of the elastic adhesive disc (110), for indenting the skin (200) of a patient without damaging the patient's skin, the at least one piston (80) upon actuation for causing an expansion of the elastic adhesive disc (110) and/or the protrusion of the discharge tube (54, 55) for tensioning the skin (200) of the patient, and the elastic adhesive disc (110), remaining on the skin (200) of the patient after the cylinder-piston unit has been taken away, can be removed separately.

2. Cylinder-piston unit with adhesive disc according to claim 1, wherein the elastic adhesive disc (110) located in the installation position (111) is at a distance of at least one millimeter from the front end face (46) of the bottom portion (33) directed towards it.

3. Cylinder-piston unit with adhesive disc according to claim 1, wherein an outer wall (57) of the discharge tube (54, 55) is shaped cylindrically at least in part.

4. Cylinder-piston unit with adhesive disc according to claim 3, wherein, the discharge tube (54) is integrally formed from the cylinder (20).

5. Cylinder-piston unit with adhesive disc according to claim 1, wherein the elastic adhesive disc (110) has a circumferential web (123) which protrudes radially which bears elastically on the inside of the front edge (59) of the annular web (51).

6. Cylinder-piston unit with adhesive disc according to claim 4, wherein the elastic adhesive disc (110) has a front blind bore (126) and a rear blind bore (127), each of the two blind bores (126) and (127) ending in a middle area of the elastic adhesive disc (110) and which lie coaxially one behind the other and which are separated by a sealing element (116) in the form of a membrane, the front blind bore (126) in the application position (111) having a diameter that is smaller than the diameter of the rear blind bore (127) with the discharge tube (54) in operative arrangement therewith.

7. Cylinder-piston unit with adhesive disc according to claim 6, wherein, the adhesive coating (121) is omitted in the area of the front blind bore (126).

8. Cylinder-piston unit with adhesive disc according to claim 1, wherein the discharge tube (55) is metallic.

9. Cylinder-piston unit with adhesive disc according to claim 8, wherein the adhesive coating (121) has a central recess (124) having a diameter greater than an external diameter of the discharge tube (55).

10. Cylinder-piston unit with adhesive disc according to claim 8, wherein the discharge tube (55) has a tapering (63) proximate an outlet nozzle (60).

11. Cylinder-piston unit with adhesive disc according to claim 1, the elastic adhesive disc (110) further including a stiffening disc (119) encapsulated or vulcanized therein.

12. Cylinder-piston unit with adhesive disc according to claim 4, wherein the discharge tube (54) at a front end (58) thereof has an about spherically curved front face (58).

* * * * *